United States Patent

Plant Pat. 3,981
Patented Nov. 16, 1976

3,981

STRAWBERRY PLANT

Royce S. Bringhurst, Davis, and Victor Voth, Santa Ana, Calif., assignors to The Regents of the University of California, Berkeley, Calif.

Filed Oct. 23, 1975, Ser. No. 625,333
Int. Cl.[2] A01H *5/03*
U.S. Cl. Plt.—48 1 Claim

This invention relates to a new and distinct variety of strawberry plant designated as "Aiko."

"Aiko" originated in 1964 as a hybrid between Cal. 46.5–1 (one of the parents of "Tufts," U.S. Plant Pat. 3,561) and Cal. 59.51–11 (a "Lassen"-"Solana" derivative), and fruited first and was selected at the University of California South Coast Field Station, Santa Ana, Calif. in 1965. At that time it was designated Cal. 63.125–39 and all testing has been completed under that number.

"Aiko" has been tested extensively at various university facilities throughout the State of California under strict controls. Meristem originated, virus-negative stock has been developed at the university, asexually reproduced and multiplied.

Figure 1:
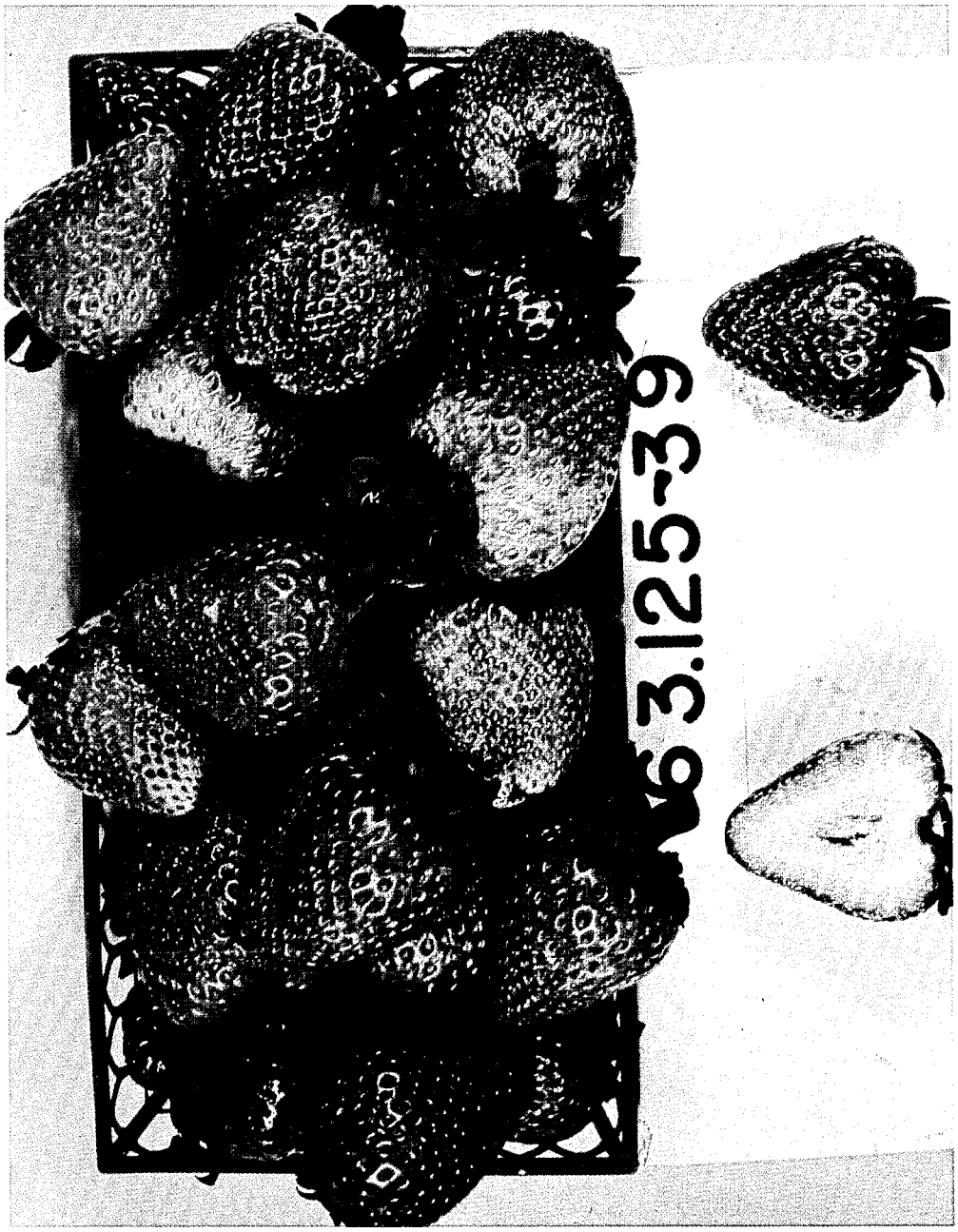
Figure 2:
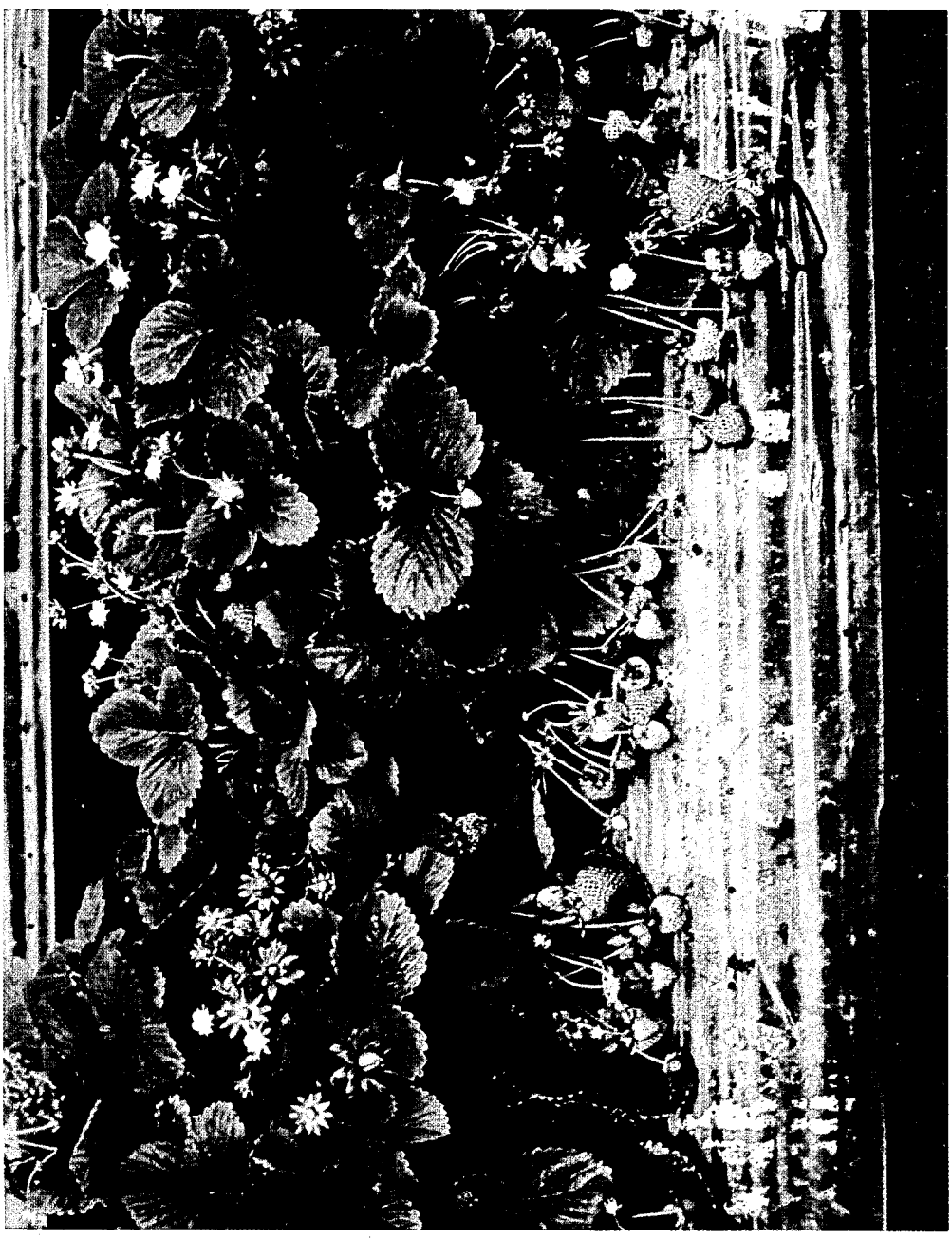

Typical plant, flower and fruit characteristics are presented in the accompanying photographic color reproductions in which FIG. 1 shows medium long conic fruit, one of which is in cross section and in which FIG. 2 shows typical springtime leaves, plant, flower and fruiting habit of summer planting in the southern areas of California.

"Aiko" is a high yielding variety comparable to "Tufts," U.S. Plant Pat. 3,561, or "Tioga" on the summer planting system. It starts later than either and longer and the fruiting peaks are less pronounced.

The dessert quality of "Aiko" fruit is equal to or better than "Tioga" or "Tufts." According to tests, the fruit has averaged higher in soluble solids than "Tioga" or "Tufts" although the difference is not significant. "Aiko" fruit has averaged significantly higher in ascorbic acid (vitamin C) than "Tioga" or "Tufts" fruit, namely 79 mg./100 grams of fresh fruit as opposed to 48 mg./100 grams and 58 mg./100 grams of fresh fruit respectively for the other two cultivars. Fully ripe fruit should process well.

"Aiko" is well adapted and should be very useful for summer planting in the central coast area, particularly in the Watsonville, Salinas and San Jose areas of California. It should also be successful in the Santa Maria, Calif. area. It is too late in bearing for south coastal California. It should be planted with "Tufts." Results with winter plantings have been disappointing.

The varietal characteristics of this new strawberry plant described below in detail were observed upon its discovery and subsequently through its test period.

DESCRIPTION

Plants

"Aiko" plants are small to medium in size, smaller and less erect in growth habit than those of either "Tioga" or "Tufts." The plants are about as vigorous as those of "Tufts" and require about the same amount of nitrogen fertilization. They have a slightly higher chilling requirement than plants of "Tufts" or "Tioga." "Aiko" plants are about as susceptible to Verticillium Wilt as those of "Tufts" or "Tioga" and are about as tolerant of salinity. Foliar diseases such as mildew or leafspot appear to be less of a problem than with "Tufts" or "Tioga." "Aiko" runners prolifically and propagates at least as well as "Tufts" which is considerably better than "Tioga."

Flowering and flowers

"Aiko" is a standard short-day type that commences flowering later than "Tioga" or "Tufts." "Aiko" persists in fruiting relatively evenly throughout the late spring, summer and early fall in the Watsonville area, much more so than "Tioga" and significantly more so than "Tufts" in summer plantings.

Flowers are borne on medium length panicles, much shorter than those of "Tufts" but the fruit is even more exposed than that of "Tufts" because the plants are smaller. Flowers are self fruitful with an abundance of pollen and they set well under a variety of conditions.

Fruit

The medium long conic fruit is almost round in cross section and it varies much less than "Tioga" fruit throughout the season. Under certain conditions the tip of some of the fruit fails to develop normally and "buttons off." This is similar to the problem with "Aliso" but less serious because the fruit is longer.

The ripe color is a bright slightly orange-red which deepens to full red as the fruit ages, similar to "Tioga" and "Tufts." Internally, the color is about like that of "Tioga," a little lighter than "Tufts" and the flesh is about as firm as that of "Tioga."

The skin is about as tough as that of "Tioga" and it handles and ships about as well. The achenes are slightly more embedded than those of "Tioga."

"Aiko" fruit averages about the same size as that of "Tufts" although the largest fruit is not as large as the largest borne by "Tioga" or "Tufts." The size is generally more uniform with few fruits too small for fresh market if the plants are healthy.

We claim:

1. The new and distinct variety of strawberry plant herein described and illustrated, and identified by the characteristics enumerated above.

No references cited.

ROBERT E. BAGWILL, Primary Examiner